(12) United States Patent
Pei et al.

(10) Patent No.: US 8,500,990 B2
(45) Date of Patent: Aug. 6, 2013

(54) ELECTROCHEMICAL BIOSENSORS BASED ON NAD(P)-DEPENDENT DEHYDROGENASE ENZYMES

(75) Inventors: Jianhong Pei, Boxborough, MA (US); Chung Chang Young, Weston, MA (US)

(73) Assignee: Nova Biomedical Corporation, Waltham, MA (US)

( * ) Notice: Subject to any disclaimer, the term of this patent is extended or adjusted under 35 U.S.C. 154(b) by 740 days.

(21) Appl. No.: 12/427,994

(22) Filed: Apr. 22, 2009

(65) Prior Publication Data

US 2010/0270175 A1    Oct. 28, 2010

(51) Int. Cl.
   *G01N 27/327*   (2006.01)
   *G01N 27/26*    (2006.01)
   *B05D 5/12*     (2006.01)

(52) U.S. Cl.
   USPC ............... 205/777.5; 204/403.14; 435/287.1; 205/787; 205/792; 422/68.1

(58) Field of Classification Search
   USPC ................... 204/400–403.15; 205/787, 792, 205/777.5, 778; 435/287.1; 422/68.1
   See application file for complete search history.

(56) References Cited

U.S. PATENT DOCUMENTS

| | | | |
|---|---|---|---|
| 4,254,222 A | 3/1981 | Owen | |
| 4,351,899 A | 9/1982 | Owen | |
| 5,326,697 A | 7/1994 | Magers | |
| 5,510,245 A | 4/1996 | Magers | |
| 5,912,139 A | 6/1999 | Iwata et al. | |
| 6,287,451 B1 | 9/2001 | Winarta et al. | |
| 6,541,213 B1 | 4/2003 | Weigl et al. | |
| 6,541,216 B1 | 4/2003 | Wilsey et al. | |
| 6,736,957 B1 * | 5/2004 | Forrow et al. | 205/777.5 |
| 6,767,441 B1 | 7/2004 | Cai et al. | |
| 6,837,976 B2 | 1/2005 | Cai et al. | |
| 6,863,800 B2 | 3/2005 | Karinka et al. | |
| 6,863,880 B2 | 3/2005 | Caniggia et al. | |
| 6,984,307 B2 | 1/2006 | Zweig | |
| 2007/0131549 A1 * | 6/2007 | Cai et al. | 204/403.02 |
| 2008/0073207 A1 * | 3/2008 | Teodorczyk et al. | 204/403.14 |
| 2009/0186372 A1 * | 7/2009 | Bell et al. | 435/26 |

OTHER PUBLICATIONS

Forrow, Nigel J. et al., Development of a commercial amperometric biosensor electrode for ketone D-3-hydroxybutyrate, Biosensors and Bioelectronics, Aug. 17, 2004, 1617-1625, 20, Elsevier, UK.

* cited by examiner

*Primary Examiner* — J. Christopher Ball
*Assistant Examiner* — Jennifer Dieterle
(74) *Attorney, Agent, or Firm* — Robert R. Deleault, Esq.; Mesmer & Deleault, PLLC

(57) ABSTRACT

A biosensor for measuring an analyte in a liquid sample includes a working electrode having a dispensed reagent thereon wherein the dispensed reagent contains an enzyme capable of catalyzing a reaction involving the analyte, a mediator that is considered an enzyme inhibitor, and an enzyme co-factor where the working electrode provides a stable and sensitive response even when the biosensor is stored at ambient conditions for a period of time selected from the group consisting of at least 3 months, 12 months and two years or more.

30 Claims, 8 Drawing Sheets

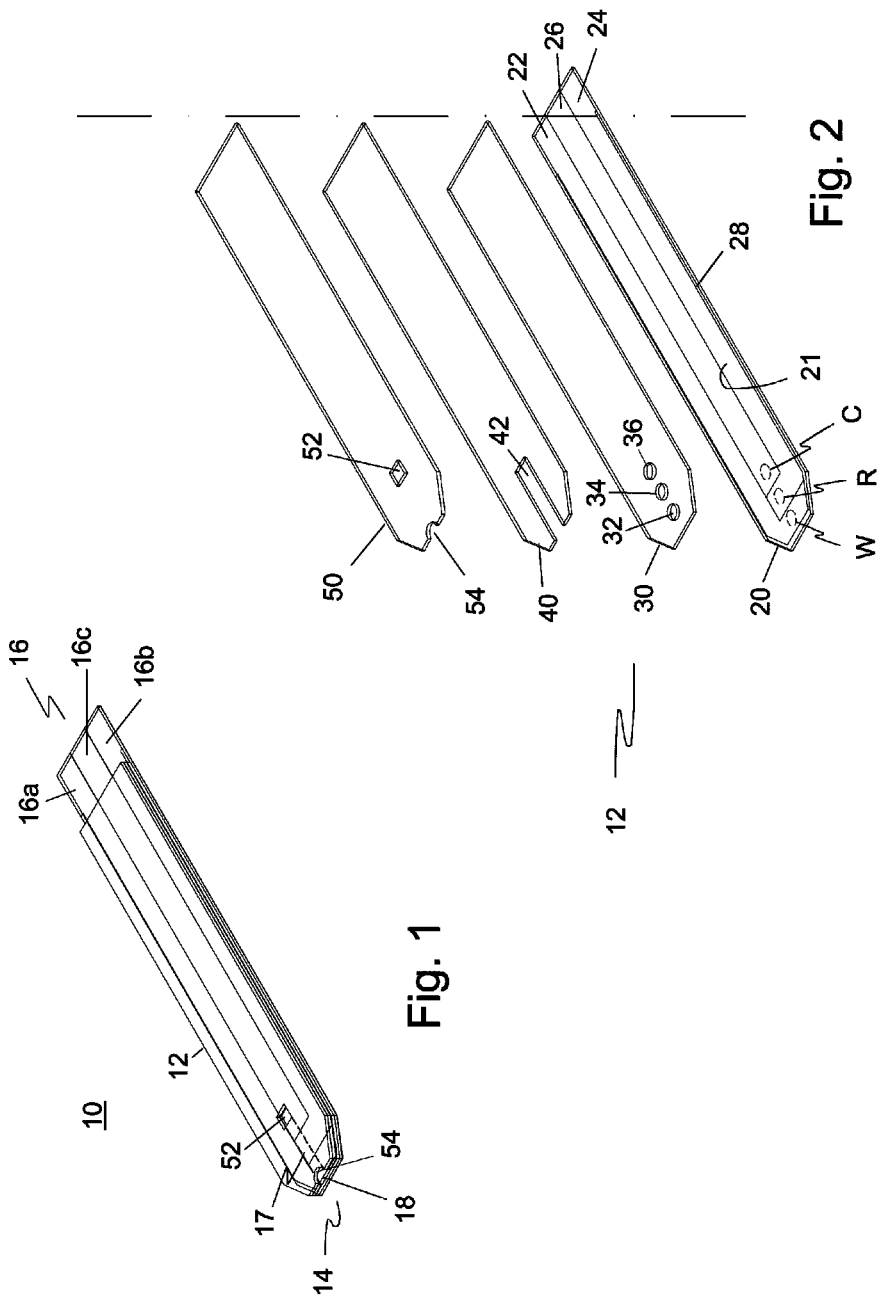

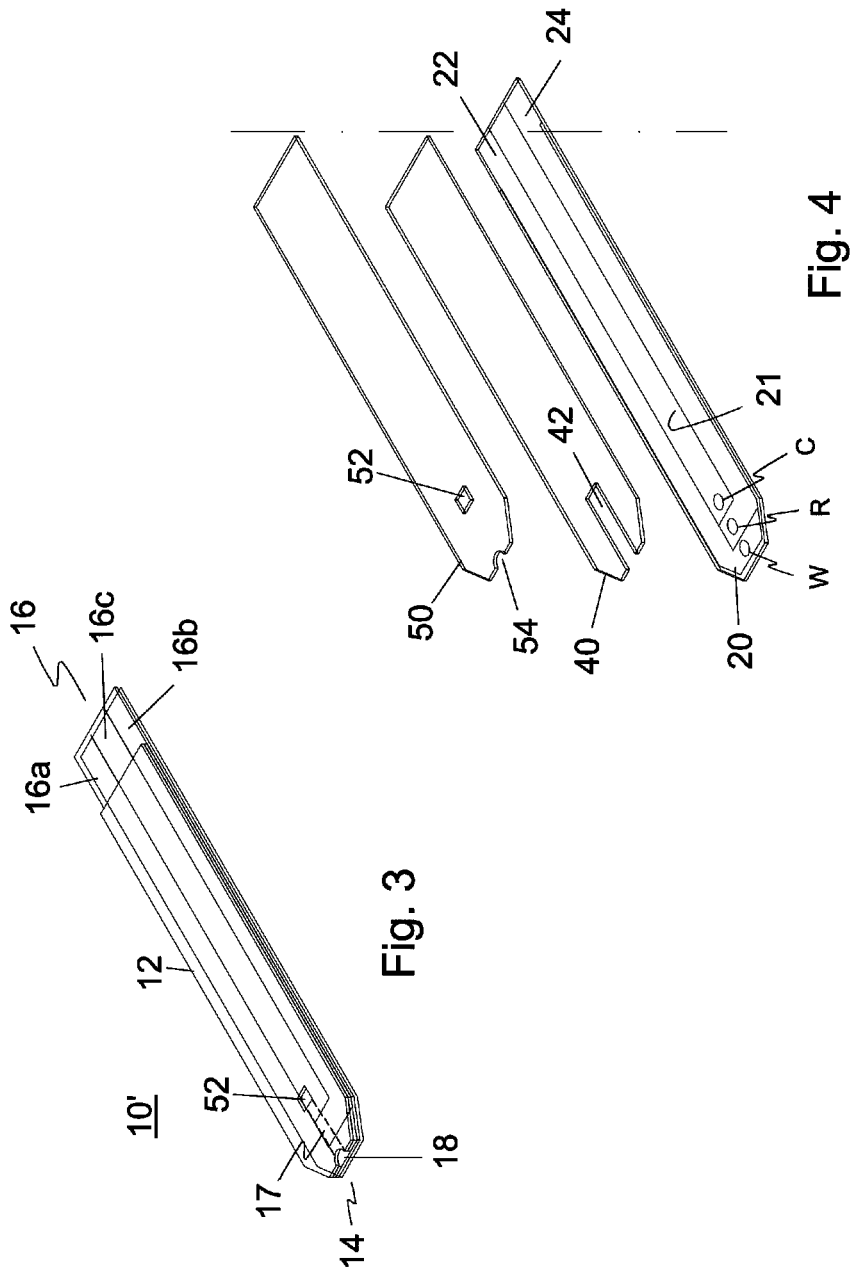

ELECTROCHEMICAL BIOSENSORS BASED ON NAD(P)-DEPENDENT DEHYDROGENASE ENZYMES

BACKGROUND OF THE INVENTION

1. Field of the Invention

The present invention relates generally to an electrochemical biosensor for quantification of a specific component or analyte in liquid sample. Particularly, the present invention relates to a disposable electrochemical-based sensor for measuring the concentration of analytes in biological fluids such as plasma, serum, whole blood or the like. More particularly, the present invention relates to an electrochemical-based sensor that uses compounds as mediators for the recycling of cofactors used in the sensor.

2. Description of the Prior Art

The most common, commercially-available, amperometric biosensors are based on oxidase enzymes such as glucose oxidase, lactate oxidase, and the like. These biosensors commonly use oxygen or other mediators such as ferrocene, ferricyanate, etc., as electron acceptors that recycle the enzymes after substrate reaction. The use of dehydrogenase enzymes in biosensors, however, offer some advantages over the oxidase enzymes where the dehydrogenase enzyme-based biosensors are unaffected by oxygen during the measurement.

In recent years, analytical detection in physiological fluids, e.g. blood, urine, sweat, serum, plasma etc., is of ever increasing importance in a variety of applications including clinical laboratory testing, home testing, etc. These kinds of tests have a great impact on the diagnosis and management of various disease conditions. The development of the glucose biosensor is one of the most successful testing devices to date. Although blood glucose is clearly the most important clinical parameter to be measured in the monitoring of diabetes, it is not the only parameter of clinical interest. Other measurements of medical relevance include glycosylated hemoglobin and ketone bodies. Glycosylated hemoglobin is an indicator of long-term blood glucose levels while the level of ketone bodies is an indicator of diabetic ketoacidosis (DKA) of a patient.

The concentration of ketone bodies present in urine and blood of healthy people is very low and negligible. The presence of an excess amount of ketone bodies in blood is called ketosis. The presence of an excess amount of ketone bodies in urine is called ketonuria. Diabetes mellitus is the most common disorder associated with ketosis or ketonuria. If diabetes mellitus is untreated or inadequately treated, an excess amount of ketone bodies will accumulate in the blood, i.e ketosis, and excreted into the urine, i.e. ketonuria. This condition is called diabetic ketoacidosis (DKA). DKA is a potential life-threatening condition that occurs mostly in Type 1 diabetes, though it is also known to occur in Type 2 diabetes. Poor metabolism of high carbohydrate levels derived from insulin deficiency can result in the accumulation of ketone bodies, which is a metabolic by-product of fatty acid metabolism. Ketone bodies are produced within the mitochondria of hepatocytes and include β-hydroxybutyrate, acetoacetate, and acetone.

In diabetic ketoacidosis, β-hydroxybutyrate accounts for a major portion of the ketone bodies whereas acetone is only produced in small amounts from the decarboxylation of acetoacetate. β-hydroxybutyrate is present in blood at about two to three times the concentration of acetoacetate. Quantification of β-hydroxybutyrate levels in blood by monitoring diabetes mellitus and providing guidance for insulin therapy is helpful in avoiding DKA. Blood ketone testing, however, is more reliable for diagnosing and monitoring DKA. Conventional bedside tests for urine and blood ketone assessment, however, do not test for β-hydroxybutyrate. These tests are based on the nitroprusside reaction and react only with acetoacetate and, to a less extent, acetone. Misleading information may result from such conventional tests in the assessment of DKA.

The detection of diabetic ketoacidosis in an individual with diabetes mellitus is important and often indicates that a change in insulin dosage or other treatment is necessary. The conventional bedside tests for urine ketone assessment includes test strips provided under the trademarks Ketostix® and Keto-Diastix® (Bayer) or Chemstrip® K (Roche). Such test strips are based on non-enzyme based methods such as the nitroprusside reaction and only react with acetoacetate and to a lesser extent, acetone. These conventional test strips do not respond to β-hydroxybutyrate, which is the major concentration of ketone bodies. A disadvantage of these conventional tests is that the urine assay for ketones possesses a natural delay in detecting blood ketosis. Consequently, a urine assay for acetoacetate is insufficient to monitor the onset of ketosis in a diabetic individual. The presence of β-hydroxybutyrate in the blood indicates the onset of ketosis much earlier than the detection of acetoacetate in the urine, and is a much more accurate test for monitoring the presence of ketone bodies and, hence, the effectiveness of a particular insulin therapy.

There is an increasing need for measuring β-hydroxybutyrate, which is a dominant species of ketone bodies, in blood samples for the early and effective diagnosis of the onset of DKA. Simple, dry reagent, whole blood tests for β-hydroxybutyrate, the most clinically relevant indicator of ketoacidosis, are known in the art. A widely-used colorimetric test involves the reduction of colorless dye 2-(4-indophenyl)-3-(4-nitropheyl)-5-phenyltetrazolium chloride hydrate by β-hydroxybutyrate to produce a colored formazan compound. This common dye, however, is not stable and highly photosensitive. It also responds to ascorbate and glutathione. U.S. Pat. No. 4,254,222 (1981; Owen) and U.S. Pat. No. 4,351,899 (1982; Owen) disclose an assay for β-hydroxybutyrate where 3-hydroxybutyrate is oxidized to acetoacetate by β-hydroxybutyrate dehydrogenase (HBDH) in the presence of nicotinamide adenine dinucleatide (NAD$^+$). The reduced NADH produced from this reaction, in turn, reacts with a tetrazolium dye to form a colored formazan compound. The degree and intensity of the color transition correlates to the concentration of β-hydroxybutyrate in the sample solutions.

U.S. Pat. No. 5,510,245 (1996; Magers) and U.S. Pat. No. 5,326,697 (1994; Magers) disclose an improved calorimetric method that utilizes a reductive pathway based on lipoamide dehydrogenase (LADH) and a thiol-sensitive indicator dye such as Ellman's reagent. It was found the NADH, produced from the β-hydroxybutyrate dehydrogenase enzyme reaction, can interact with lipoamide dehydrogenase (LADH) and D,L-lipoamide to form a thiol compound (6,8-dimercaptooctamide). The 6,8-dimercaptooctamide then interacts with a thiol-responsive indicator dye such as Ellman's reagent. Upon reaction, the thiol-sensitive indicator dye undergoes a detectable color transition that can be used to measure the level of 3-hydrobutyrate in the blood sample.

The colorimetric methods for 3-hydrobutyrate suffer the disadvantages of poor stability, interference from co-existing species such as ascorbate, glutathione etc. in the blood, and insufficient sensitivity and accuracy.

NAD- and NADP-dependent enzymes are of great interest insofar as many have substrates of clinical value, such as glucose, D-3-hydroxybutyrate, lactate, ethanol, and cholesterol. Amperometric electrodes for detection of these substrates and other analytes can be designed by incorporating this class of enzymes and establishing electrical communication with the electrode via the mediated oxidation of the reduced cofactors NADH and NADPH.

NAD- and NADP-dependent enzymes are generally intracellular oxidoreductases. The oxidoreductases are further classified according to the identity of the donor group of a substrate upon which they act. The category of oxidoreductases is also broken down according to the type of acceptor utilized by the enzyme. The enzymes of relevance have $NAD^+$ or $NADP^+$ as acceptors. These enzymes generally possess sulphydryl groups within their active sites and hence can be irreversibly inhibited by thiol-reactive reagents such as iodoacetate. An irreversible inhibitor forms a stable compound, often through the formation of a covalent bond with a particular amino acid residue that is essential for enzymatic activity.

U.S. Pat. No. 6,541,216 (2003; Wilsey et al.) discloses a biosensor and method to test blood ketone bodies using an amperometric meter. The test strip has a reagent that is reactive with β-hydroxybutyrate in sample solution to generate an electrical output signal, which is related to the concentration of β-hydroxybutyrate in the sample solution. The reagent in this method includes ferricyanide salt as mediator, β-hydroxybutyrate dehydrogenase as the first enzyme operative to catalyze the oxidation of β-hydroxybutyrate, $NAD^+$ as a cofactor corresponding to the first enzyme, and diaphorase as the second enzyme operative to catalyze the oxidation of a reduction form of the cofactor (NADH). The oxidation form of the mediator will accept the electron from the second enzyme and generates an electrical signal at the electrode surface, which is related to the concentration level of β-hydroxybutyrate.

U.S. Pat. No. 6,736,957 (2004; Forrow et al.) and a research paper (N.J. Forrow et.al, Biosensors & Bioelectronics, 2005, 20, 1617-1625) disclose an amperometric biosensor for β-hydroxybutyrate based on the discovery of $NAD^+$ and $NADP^-$ mediator compounds that do not bind irreversibly to thiol groups in the active sites of intracellular dehydrogenase enzymes. These mediator compounds such as 1,10-phenanthroline quinone (1,10-PQ), which is used as an electron mediator in their electrochemical measurement system, can increase the stability and reliability response in amperometric electrodes constructed from NAD- and NADP-dependent enzyme. The dry reagents include 1,10-phenanthroline quinone (1,10-PQ), β-hydroxybutyrate dehydrogenase and NAD+ as the cofactor. This sensor shows reliable and sensitive response to the concentration levels of β-hydroxybutyrate in blood samples. Meldola's Blue (MB) was also studied as a mediator in the system, but it was found that MB did not work well in their electrochemical test system due to the inhibition of β-hydroxybutyrate dehydrogenase enzyme activity by MB and poor long term stability of the test strips.

The dehydrogenase enzymes such as, for example, glucose dehydrogenase, D-3-hydroxybutyrate dehydrogenase (HBDH), and lactate dehydrogenase et.al are known to be common dehydrogenases for construction of biosensors. As disclosed by Forrow et al., there are certain mediators that are considered efficient mediators for NADH but are irreversible enzyme inhibitors such as Meldola's blue, 4-methyl-1,2-benzoquinone (4-MBQ), 1-methoxy phenazine methosulphate (1-Meo-PMS) and 2,6-dichloroindophenol (DCIP), which cause losing the activity of enzymes, insensitive response and poor stability in sensors containing dehydrogenase enzymes.

SUMMARY OF THE INVENTION

The present invention provides a new and improved composition, test device and method of determining the presence and concentration of an analyte in human fluids using a biosensor capable of long term storage that contains a mediator originally considered to be an irreversible enzyme inhibitor. The present invention is based on the discovery that a mediator originally considered to be an irreversible enzyme inhibitor can be used to construct a biosensor containing a dehydrogenase enzyme that displays a very sensitive and stable response to the concentration of an analyte in a liquid sample even after long term storage, e.g. 12 months or more.

The present invention further provides a test device and method of determining the presence and concentration of analytes in human fluids. In one embodiment, the biosensor includes a working electrode and a reference electrode. The working electrode has a reagent matrix formed thereon from a dispensing reagent containing an enzyme capable of catalyzing a reaction involving the analyte, a mediator that is originally considered an irreversible enzyme inhibitor, and an enzyme cofactor where the biosensor is capable of producing a stable and sensitive response even when the sensor is stored at ambient conditions for more than 3 month, preferably for more than 12 months, more preferably for more than 2 years.

In another embodiment of the present invention, the ratio of the enzyme cofactor to the mediator is in the range of about 0.01:1 to 15:1. The enzyme cofactor is further present in the dispensing reagent in an amount of less than 5% (w/w) and, preferably, in an amount in the range of about 0.01% to about 3.0%.

In a further embodiment, the mediator has a concentration in the dispensing reagent of about 2.0% (w/w) or less and, preferably, in the range of about 0.2% to about 1.0% (w/w).

In still another embodiment of the present invention, the mediator is one of meldola's blue, 1-methoxy phenazine methosulfate, 4-methyl-1,2-benzoquinone, and 2,6-dichloroindophenol.

The present invention further provides a new and improved composition, test device and method of determining the presence and concentration of ketone bodies in human fluids. In one embodiment, the present invention features a test element for an amperometric biosensor. The test element includes an electrode with test reagents disposed thereon. The test reagents form a reagent matrix that includes a redox mediator considered to be an irreversible enzyme inhibitor, an enzyme capable of catalyzing a reaction involving the β-hydroxybutyrate, and an enzyme co-factor such as $NAD^+$ and $NADP^+$.

In another embodiment, the present invention is based on the discovery that a redox mediator considered to be an irreversible enzyme inhibitor such as, for example, 8-Dimethylamino-2,3-benzophenoxazine hemi(zinc chloride) salt, also known as Medola's Blue (MB), can be used to construct a biosensor that displays a very sensitive and stable response to the concentration of β-hydroxybutyrate in a sample solution without inhibiting the enzyme activity of an enzyme capable of catalyzing a reaction involving the β-hydroxybutyrate.

In another embodiment, the present invention features a disposable sensor strip for detecting an analyte such as β-hydroxybutyrate, glucose, glucose 6-phosphate, cholesterol, ethanol, lactate, glycerol, malate, and fructose in a liquid sample. The strip includes a laminated body having a sample inlet end and an electrical contact end, a sample inlet, a sample chamber in communication between the sample inlet and a vent opening, a working electrode with a reagent matrix disposed thereon, and reference electrode. The reagent matrix includes a mediator that is considered to be an irreversible enzyme inhibitor such as, for example, 8-Dimethylamino-2, 3-benzophenoxazine hemi(zinc chloride) salt or MB as a redox mediator, an enzyme capable of catalyzing a reaction involving the analyte, and an enzyme co-factor such as $NAD^+$ and NADP$^+$. The strip may optionally include a third electrode or compensating electrode for background and interference correction when the liquid sample is a blood sample.

In yet another embodiment, the present invention provides a biosensor based on NAD(P)-dependent dehydrogenase enzymes that includes a working electrode having a reagent matrix containing a mediator that is considered an irreversible enzyme inhibitor, and a reference electrode. The working electrode is capable of measuring the concentration of an analyte in a liquid sample without calibrating the working electrode.

In a further embodiment of the present invention, the biosensor based on NAD(P)-dependent dehydrogenase enzymes includes a reagent matrix where the NAD(P)-dependent dehydrogenase enzymes and the mediator are in a ratio in the range of about 0.01:1 to 15:1.

The reference electrode may incorporate any reference material, including, but not limited to, silver-silver chloride, a redox mediator or other reference electrode materials. The optional compensating electrode incorporates a reagent matrix similar to that of the working electrode, but without the enzyme.

A NAD-dependent enzyme that can be used in the present invention includes several dehydrogenases. The dehydrogenases for use in the present invention act in a specific fashion on the substances to be measured by one or several enzyme reactions. Several examples of these combinations include, but are not limit to, glucose dehydrogenase for glucose, glucose 6-phosphate dehydrogenase for glucose 6-phosphate, β-hydroxybutyrate dehydrogenase for β-hydroxybutyrate, cholesterol dehydrogenase for cholesterol, lactate dehydrogenase for lactate, alcohol dehydrogenase for ethanol, glycerol dehydrogenase for glycerol, malate dehydrogenase for malate and fructose dehydrogenase for fructose.

As an example, β-hydroxybutyrate dehydrogenase (HBDH) is a NAD-dependent enzyme which can specifically catalyze the oxidation of β-hydroxybutyrate (β-HB) in the presence of NAD$^+$ as co-factor and the reaction can be described as follow:

(1)

$$\beta-hydroxybutrate + NAD^+ \xrightarrow{HBDH} Acetoacetate + NADH + H^+$$

Although NADH can be oxidized at the electrode surface, a number of disadvantages are associated with the direct electrochemical oxidation of NADH. The direct electrochemical oxidation of NADH at a metallic or carbonaceous electrode is very irreversible and only proceeds at a very high overpotential. Furthermore, it has poor reproducibility and low sensitivity. A way to decrease the high overpotentials required for the NADH oxidation at a solid electrode surface and increase the electron transfer rate is to introduce an electron mediator into the working solution. An electron mediator is a redox couple which can react with the reduced enzyme co-factor (NADH) and then undergo rapid charge transfer at substantially decreased overpotential on the electrode surface. The resultant current will be related to the concentration of β-HB.

A practical and usable mediator preferably has low formal potential, is stable in both oxidized and reduced forms, and the heterogeneous electron transfer reaction should not be the rate limit step. The most effective NADH mediators currently known are those compounds which include ortho-quinones, para-quinones and quinoneimines in their basic structural elements. The representative examples of the quinoid structure type include, but are not limited to, benzo-α-phenazoxonium chloride, Meldola's Blue (MB), 3,4-methyl-1,2-benzoquinone, 1-methoxy phenazine methosulphate, 1,10-phenanthroline quinone (1,10-PQ).

MB was found to be one of several efficient mediators with NADH (Forrow et.al Biosensors and Bioelectronics, 2005, 20, 1617-1625), but it had serious disadvantages. It was found that these efficient mediators inhibited the activity of HBDH and, therefore, were not considered suitable for construction of a β-HB biosensor due to the irreversible enzyme inhibitor characteristics of these efficient mediators to the activity of HBDH enzyme. To avoid this disadvantage, it was demonstrated that even though the electron mediators known as the phenanthroline quinone mediators were relatively inefficient NADH mediators compared with the efficient but irreversible enzyme inhibitor mediators, the phenanthroline quinone mediators had no inhibition effect on the HBDH and was used as a mediator to develop a β-HB biosensor with long term stable shelf life and good accuracy.

In the present invention, it was discovered and unexpected that a biosensor displaying a very sensitive and stable response to the concentration of an analyte in the sample solution could be made using the highly efficient yet irreversible enzyme inhibitor mediators (such as MB) and NAD$^+$ cofactor in the reagent matrix. This was contrary to the conventional belief of the long term effect of the irreversible enzyme inhibitor mediators on the activity of the enzyme that is used and capable of catalyzing a reaction involving the analyte. The NADH produced from the enzyme reaction reacts with the irreversible enzyme inhibitor mediator. The NADH is oxidized to NAD$^+$ and the mediator is changed into its reduced form. If an appropriate potential is applied on the electrode surface, the reduced form of the mediator can be re-oxidized on the electrode surface and the resultant current output signal is proportional to the concentration of the analyte in the sample solution.

In the present invention, both of the concentrations and the relative concentrations of NAD$^+$ and the irreversible enzyme inhibitor mediator are critical for constructing a biosensor that has a sensitive and long term stable response. Too high a concentration of NAD$^+$ will foul the electrode surface and too low a concentration of NAD$^+$ will slow down the enzyme reaction. The concentration of NAD$^+$ in the dispensed reagent solution used to form the reagent matrix should be in the range of about 0.01% to about 3.0% (w/w), preferably about 0.1% to about 0.6%. Regarding the irreversible enzyme inhibitor mediator, too high a concentration of the irreversible enzyme inhibitor mediator will inhibit the enzyme activity of dehydrogenase and too low a concentration of mediator will create a current response that is too small. The concentration of irreversible enzyme inhibitor mediator (IEIM) in the dispensed reagent solution should be in the range of about 0.05% to about 2.0%, preferably about 0.2% to about 1.0%. The reaction between IEIM and NADH is described by the following equation.

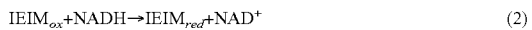

$$IEIM_{ox} + NADH \rightarrow IEIM_{red} + NAD^+$$ (2)

When the working electrode of the present invention is exposed to a liquid sample containing an analyte to be measure, the analyte in the sample solution at the working electrode region will be catalytically oxidized by an enzyme and then the cofactor NAD$^+$ will be reduced to NADH. The NADH produced in the reaction will be re-oxidized by the redox mediator IEIM, where IEIM changes from its oxidized state into its reduced state. When an appropriate and pre-defined potential is imposed across the working electrode and a reference electrode, the reduced form of IEIM will be re-oxidized to its oxidized form and a current signal at the working electrode is obtained. The obtained current signal is proportional to the concentration of the analyte in the sample fluid.

When the liquid sample is a blood sample, the hematocrit of the blood sample also influences and affects the current signal. The effect of hematocrit can be corrected by measuring the impedance (I) or resistance (R) of the blood samples. For purposes of the following equations, impedance and resistance is used interchangeably since the measurement value for the impedance or resistance is Ohms. The impedance value between the electrodes (working/reference/compensating) can be used for the correction of hematocrit. Hematocrit effect can be corrected and eliminated using the following equations:

$$H = (a_1)(R^2) + (a_2)(R) + a_3 \quad (3)$$

where R is the resistance value measured in Ohms, H is hematocrit value, and $a_1$, $a_2$ and $a_3$ are constants. The equation is approximate and it can be in different format.

The hematocrit value is then used to mathematically correct the β-HB concentration measured using the above described sensor. The following equation represents the calculation performed using the calculated hematocrit level from equation (3):

$$C_{corr} = (C_{mea}) * [b*H^2 + c*H + d] \quad (4)$$

where $C_{corr}$ is the corrected analytical concentration $C_{mea}$ is the measured analytical concentration b, c, and d are constants H is the hematocrit level calculated from equation (3)

The constant values "a" through "d" above are empirically determined using electrodes having a consistent, predefined structure. The values are dependent on several factors such as the arrangement of the electrodes, the surface area of the electrodes, and the ratio of the surface areas of the electrodes. It should be noted that the correction can also be done by using the ohmic value without converting the ohmic value to hematocrit by simply substituting equation (3) into equation (4) and creating an algorithm to correct for the presence of hematocrit in the sample fluid.

In the present invention, β-hydroxybutyrate and ethanol will be used as a model molecule for the electrochemical biosensor test strip.

BRIEF DESCRIPTION OF THE DRAWINGS

FIG. 1 is a perspective view of one embodiment of the present invention showing the test strip.

FIG. 2 is an exploded view of the embodiment in FIG. 1 showing the four component layers of the test strip.

FIG. 3 is a perspective view of another embodiment of the present invention showing the test strip.

FIG. 4 is an exploded view of the embodiment in FIG. 3 showing the three component layers of the test strip.

DETAILED DESCRIPTION OF THE PREFERRED EMBODIMENT

Figure 5:
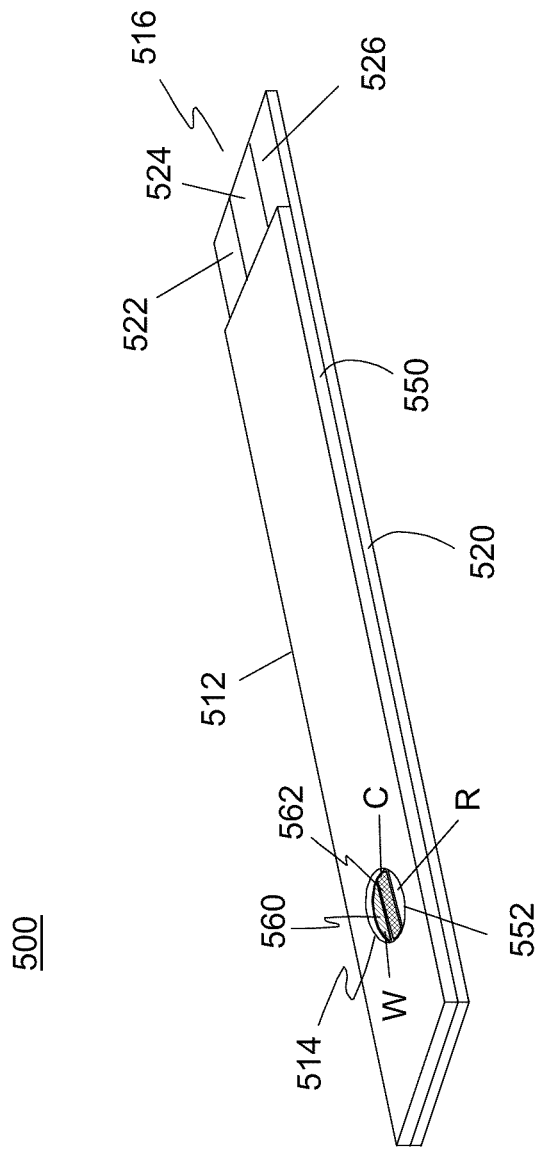
FIG. 5 is a perspective view of another embodiment of the present invention showing a test strip with a sample application well.

Enzyme biosensors of the present invention can be used in assaying for the presence of an analyte in a liquid sample. The sample can be a complex biological sample such as a biological fluid and the analyte can be a naturally occurring metabolite such as glucose, D-3-hydroxybutyrate, ethanol, lactate, cholesterol, glycerol, malate, or fructose. The biosensors of the present invention generally use a single-use strip. The single-use strip has a working electrode with a reagent matrix containing an enzyme, an enzyme co-factor, and a mediator that is originally considered an irreversible enzyme inhibitor for generating a current indicative of the level of the analyte and a reference/counter electrode. The reagent matrix can be in one or more layers associated with the working electrode.

In general, NAD(P)-dependent dehydrogenases catalyze reactions according to the equation:

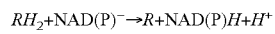

where $RH_2$ represents the analyte and R the product. In the process of the forward reaction, $NAD(P)^-$ (i.e., $NAD^+$ or $NADP^+$) is reduced to NAD(P)H. Suitable amperometric biosensors provide an electrochemical mediator that can reoxidize NAD(P)H, thereby regenerating $NAD(P)^+$. And the mediator changes from its oxidation form to its reduction form of the mediator. With appropriate potential applying at the working electrode, the reduction form of mediator can be re-oxidized at the electrode surface to generate a current that is indicative of the concentration of the analyte.

The biosensor includes an elongated electrically insulating carrier having longitudinal, substantially parallel, electrically conducting tracks. Each track is provided at the same end with means for electrical connection to a read-out and an electrode at the other end. One of the electrodes is the reference/counter electrode and another is the working electrode with test reagent. The sensor can be configured in the form of a supporting strip of electrically insulating carrier material such as a synthetic polymer carrying the working and reference electrodes supported on electrically conductive tracks between its ends. For example, the electrodes can take the form of two shaped areas side by side on the carrier strip, as shown in FIG. 2 (i.e., electrodes W and R). Such areas can be designed as a target area to be covered by a quantity of sample, such as whole blood, for testing the analyte. The sample areas can be circular, rectangular, diamond-shaped, semicircular, or triangular areas and can be employed to provide a target area for optimized contact by a liquid sample. In the preferred embodiment, the test sample completes an electrical circuit across the working electrode and the reference/counter electrode for amperometric detection of the activity of the analyte.

Other electrodes such as a compensating electrode can also be included. These other electrodes can be of similar formulation to the working electrode (i.e., with the associated test reagents), but lacking one or more of the working electrode's active components. A compensating electrode, for example, can provide more reliable results, in that if charge passed at the compensating electrode is subtracted from charge passed at the working electrode, then the resulting charge can be concluded to be due to the reaction of interest. Another advantage of the compensating electrode is to eliminate the co-existed interferent for blood test.

The reference electrode/counter electrode may be a classic silver/silver chloride electrode but it may also be identical to the working electrode in construction. In one embodiment, the two separate conductive tracks may both be coated with an appropriate formulation of enzyme, cofactor and mediator in a binder containing aqueous solution to yield a coating/reagent matrix. In those cases in which the coating is non-conductive, a common coating may overlay both electrodes. When a potential is applied one of the electrodes will function as a reference/counter electrode by absorbing the electrons liberated at the working electrode. The mediator at the reference/counter electrode will simply become reduced as a result of interaction with the electron flow at its electrode.

In a preferred embodiment of the present invention, a working electrode is produced by using a formulation which includes not only the enzyme, the enzyme cofactor and the mediator but also binder ingredients which cause the working electrode to give a more consistent response to concentrations of interest for the analyte being sensed. A reaction layer on the surface of the working electrode is provided when the sample is applied. As the mediator is reduced by reaction with the enzyme, cofactor and analyte, it is retained in close proximity to the electrode surface so that it can be readily reoxidized. The maintenance of this thin reaction layer also allows the overall analytical reaction to occur in a small volume of the overall sample.

It is critical that a given concentration of analyte results in the production of the same signal in the test for a particular electrode strip design and that the signal increases, preferably linearly, with the concentration of the analyte over the concentration range of interest. In other words, the signal is a function of the analyte concentration.

The signal may be the current observed at a fixed time after the test is initiated or it may be the current integrated over some period occurring some fixed time after the test is initiated (in essence the charge transferred over some such period). The test is conducted by covering the working electrode and a reference/counter electrode with sample and a potential applied between them. The current which then flows is either observed over some time period or measured at a set point in time after application of the potential between the electrodes. The potential may be imposed as soon as the sample covers the electrodes or it may be imposed after a short delay. The fixed time until the current or current integration is taken should be long enough to ensure that the major variable affecting the observed current is the analyte concentration.

Referring to FIG. 1, FIG. 1 illustrates one embodiment of the present invention showing a biosensor 10. The biosensor 10 has a laminated body 12, a fluid sampling end 14, an electrical contact end 16, and a vent opening 52. Fluid sampling end 14 includes a sample chamber 17 between a sample inlet 18 and vent opening 52. Electrical contact end 16 has three discrete conductive contacts 16a, 16b and 16c.

Turning now to FIG. 2, laminated body 12 includes a base layer 20, a reagent layer 30, a channel layer 40, and a cover 50. All layers of laminated body 12 are made of a dielectric material, preferably plastic. Examples of a usable dielectric material include polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene, and polystyrene.

Base layer 20 has a conductive layer 21 on which is delineated at least two, but preferably three conductive paths 22, 24 and 26. The conductive paths 22, 24, 26 may be formed by scribing or scoring conductive layer 21. In the alternative, base layer 20 may be a dielectric material on which conductive paths 22, 24, 26 are screen printed. Screen printed conductive paths may be limited to electrically conductive material or may also include an ink that contains reagent chemicals and the electrically conductive material.

Scribing or scoring of conductive layer 21 may be done by mechanically scribing the conductive layer 21 sufficiently to create the three independent conductive paths 22, 24, 26. The preferred scribing or scoring method of the present invention is done by using a laser. Conductive layer 21 may be made of any electrically conductive material such as, for example, gold, tin oxide/gold, palladium, other noble metals or their oxides, or carbon film compositions. The preferred electrically conductive material is gold or tin oxide/gold. The more preferred material for the base layer 20 is a gold-coated polyester film. An additional scoring line 28 (enlarged and not to scale; for illustrative purposes only) may be made along the outer edge of base layer 20 in order to avoid possible static problems that could give rise to a noisy signal. It should be understood, however, that scoring line 28 is not necessary to the functionality of sensor 10. The conductive layer 21 may also be done by screen printing carbon ink or carbon paste onto base layer 20 and then scribed to delineate conductive paths 22, 24, 26. Alternatively, conductive paths 22, 24, 26 may be screen printed onto base layer 20.

Reagent layer 30 has at least two, preferably three electrode openings that create electrode wells for receiving a reagent solution disclosed below. A first electrode opening 32 exposes a portion of first conductive path 22 forming a first electrode element. A second electrode opening 34 exposes a portion of second conductive path 24 forming a second electrode element. An optional third electrode opening 36 exposes a portion of third conductive path 26 forming a third electrode element. Reagent layer 30 is made of a plastic material, preferably a medical grade, one-sided adhesive tape available from Adhesive Research, Inc., of Glen Rock, Pa. or Global Instrument Corporation (GIC) (Taiwan). The thicknesses of the tape in the present invention are in the range of about 0.001 in. (0.025 mm) to about 0.01 in. (0.25 mm). The preferred thickness is about 0.003 in. (0.075 mm). Reagent layer 30 may also be (1) made from a plastic sheet and may be coated with a pressure sensitive adhesive, a photopolymer, ultrasonically-bonded to base layer 20, or (2) silk-screened onto the base layer 20 to achieve the same results as using the polyester tape mentioned.

The size of the electrode openings is preferred to be made as small as possible in order to make sample chamber 17 of sensor 10 as short as possible to minimize the volume of sample required for each test measurement. The three electrode openings 32, 34 and 36 are aligned with each other and are spaced about 0.01 in. (0.25 mm) to about 0.05 in. (1.27 mm) from each other. The use of circular electrode openings are for illustrative purposes only. It should be understood that the shape of the electrode openings and the distance between each of the electrodes is not critical. In fact, the electrode openings may differ in surface area from each other so long as the ratio of the surface areas remains substantially constant from one sensor to another.

The positional arrangement of the working (W), compensating (C) and reference (R) electrodes in sample channel 17 is not critical for obtaining usable results from sensor 10. The possible electrode arrangements within sample fluid channel 17 may be W-C-R, W-R-C, R-W-C, C-W-R, C-R-W, or R-C-W, with the arrangement listed as the electrodes would appear from the sample inlet 18 of laminated body 12 to the vent opening 52. The preferred position was found to be W-R-C.

The three electrodes W, R, C are each in electric contact with separate conductive paths 22, 24, 26. Conductive paths 22, 24, 26 terminate and are exposed for making an electrical connection to an electronic reading device on the end opposite from the sample inlet 18 of laminated body 12.

The first, second and third electrode elements have disposed thereon a reagent matrix forming the working electrode (W), the reference/counter electrode (R), and the compensating electrode (C). Preferably, the reagent matrix for the working electrode W includes an enzyme, an enzyme co-factor, an electron mediator that is considered an irreversible enzyme inhibitor and a polymer binder. For a ketone body sensor, the enzyme is preferably β-hydroxybutyrate dehydrogenase (HBDH), the co-factor is $NAD^+$, and electron mediator is Meldola's Blue (MB). The reagent matrix for the optional, compensating electrode (C) is similar in chemistry to the reagent matrix of working electrode W, but without an enzyme. One or more chemical components such as additional polymers, stabilizers, and bulking agents may be optionally included in the reagent matrix. The reagent matrix for the reference electrode R can be the same as working electrode or at least includes a redox mediator. For example, meldola's blue, or potassium ferricyanide, or a mixture of potassium ferricyanide and potassium ferrocyanide may be used to make the reference electrode function when using the preferred conductive coating material. In the alternative, the reagent matrix for the reference electrode R may be a Ag/AgCl layer (e.g., by applying Ag/AgCl ink or by sputter-coating (a) a Ag layer followed by chloridizing the Ag or (b) a Ag/AgCl layer or other reference electrode materials that do not require a redox mediator to function properly.

Channel layer 40 has a channel notch 42 located at the fluid sampling end 14. The length of channel notch 42 is such that when channel forming layer 40 is disposed onto reagent layer 30, electrodes W, R and C are within the space defined by channel notch 42. The length, width and thickness of the channel notch 42 define the volume of sample chamber 17.

Channel layer 40 is made of a plastic material, preferably a medical grade, double-sided pressure-sensitive adhesive tape available from Adhesive Research, Inc., of Glen Rock, Pa. or Global Instrument Corporation (Taiwan). The thickness of the tape is preferably in the range of about 0.001 in. (0.025 mm) to about 0.010 in. (0.25 mm). Channel notch 42 can be made with a laser or by die-cutting (the preferred method). The length of channel 42 is about 0.200 in. (5.08 mm) to about 0.250 in. (6.35 mm), and the width is about 0.05 in. (1.27 mm) to about 0.07 in. (1.778 mm). It should be understood that the thickness and the size of channel notch 42 are not critical and can be varied according to the size of the electrode areas and their spatial configuration within the test chamber.

Cover 50, which is disposed onto channel layer 40, has vent opening 52 spaced from fluid sampling end 14 of sensor 10 to ensure that the sample in the sample chamber 17 will completely cover electrode areas W, R and C. Vent opening 52 is positioned in cover 50 so that it will expose a portion of and partially overlay channel notch 42 at or near the closed end of channel notch 42. Vent opening 52 may be any shape and size but is illustrated as a rectangle having dimensions of about 0.08 in. (2 mm) by about 0.035 in. (0.9 mm). The preferred material for cover 50 is a polyester film. Transparency films from 3M or from GIC are preferred for forming cover 50. Cover 50 may optionally include an inlet notch 54 to prevent an inadvertent occlusion of sample inlet 18 (which can prevent the proper transfer of the sample fluid to the electrodes) when applying a blood sample to sample chamber 17.

FIG. 3 illustrates another embodiment of a laminated sensor 10' of the present invention. Like the 4-layer embodiment, sensor 10' has a laminated body 12, a fluid sampling end 14, an electrical contact end 16, and a vent opening 52. Fluid sampling end 14 includes a sample chamber 17 between a sample inlet 18 and vent opening 52. Electrical contact end 16 has at least two and preferably three discrete conductive contacts 16a, 16b and 16c.

As can be seen from FIG. 4, laminated body 12 includes a base layer 20, a channel layer 40, and a cover 50. As noted earlier, all layers of laminated body 12 are made of a dielectric material, preferably plastic. Unlike the 4-layer embodiment, there is no separate reagent layer in the 3-layer embodiment. Channel layer 40 also delineates the area in which a predetermined amount of reagent is disposed onto the conductive path 22 and optionally disposed onto conductive path 24. The reagent is disposed as a distinct drop or droplet on the working electrode W and the optional compensating electrode C. Reference electrode R may be any type of reference electrode previously described such as a Ag/AgCl electrode, a redox mediator electrode or other reference electrode materials and even the same as the working electrode reagents.

Turning now to FIG. 5, there is illustrated yet another embodiment of the present invention showing a sensor 500. Sensor 500 has a laminated body 512, a sample receiving well 514 and an electrical contact end 516. Laminated body 512 has a base layer 520 and a cover 550. Cover 550 has a sample opening or inlet 552 that forms, when combined with base layer 520, sample receiving well 514. Base layer 520 has at least two but preferably three electrical paths 522, 524 and 526, each of which has a first portion exposed at electrical contact end 516 for connection to a meter device (not shown) and a second portion exposed by sample receiving well 514.

The second portion of electrical paths 522, 524 and 526 exposed by sample receiving well 514 create at least a working electrode W, at least a reference/counter electrode R and an optional compensating electrode C. As previously disclosed, preferably, the reagent matrix disposed on the working electrode W includes an enzyme, an enzyme co-factor, an electron mediator that is considered an irreversible enzyme inhibitor and a polymer binder. Preferably, the enzyme is one of the dehydrogenases previously described such as, for example, β-hydroxybutyrate dehydrogenase (HBDH), the co-factor is $NAD^+$, and the electron mediator considered to be an irreversible enzyme inhibitor such as, for example, Meldola's Blue (MB). The reagent matrix disposed on the optional compensating electrode C is preferably similar in chemistry to the reagent matrix of working electrode W, and preferably without an enzyme and an enzyme co-factor. One or more chemical components such as additional polymers, stabilizers, and bulking agents may be optionally included in the reagent matrix. The reagent matrix disposed on the reference electrode R includes any reference material previously disclosed. In this embodiment of the present invention, sample receiving well 514 serves as both the sample inlet and the sample chamber for receiving a fluid sample such as blood for the determination of an analyte.

It should be understood that the conduit paths in any of the embodiments disclosed herein may be made from any non-corroding metal. Carbon deposits such as for example carbon paste or carbon ink may also be used as the conduit paths, all as is well known by those of ordinary skill in the art. The reagent matrices can also be deposited on the electrode elements in one or more ink-based layers. The reagents can be mixed with carbon ink or carbon paste and be screen-printed onto the electrode elements.

The following example is one embodiment of a biosensor of the present invention incorporating a redox mediator considered to be an irreversible enzyme inhibitor.

Chemical Reagents

Enzyme and Enzyme Co-Factor

The sensor 10 of the present invention includes at least agents in the reagent matrix of the working electrode W that can specifically react with β-HB in the sample solution. The chemical agents are preferably a β-HB sensitive enzyme and its co-factor, and, more preferably, β-hydroxybutyrate dehydrogenase (HBDH) and its co-factor $NAD^+$, in which HBDH in the presence of $NAD^+$ can selectively react with β-HB in the sample fluid. A commercially available HBDH from Toyobo and a commercially available $NAD^+$ from Sigma, USA are preferably used for the preparation of the reagent matrix for the β-HB working electrode. The concentration of $NAD_+$ in the reagent solution is in a range of about 0.01% to about 3.0%, preferably about 0.1% to about 0.6%.

Mediator

It is preferable to use a redox mediator in its oxidized form. It is also desirable that the reduced form of the mediator is capable of being oxidized electrochemically at the electrode surface at a pre-defined applied potential. It is further desirable that both of the oxidized form and reduced form of the electron mediator is stable in the reagent matrix. The redox mediator can be selected from, but is not limited to, compounds which include ortho-quinones, para-quinones, and quinoneimines in their basic structural elements. Examples of usable redox mediators include MB,1,10-PQ, indophenols, phenazines, phenothiazine, 2,6-dichloroindophenol, toluidine blue O and other compounds such as ferrocene, ferricyanide and other metallic complexes. The preferred mediator is one of the originally considered as irreversible enzyme inhibitors such as MB, which is one of the most effective electron mediators relative to the reaction with NADH. The concentration of redox mediator in the reagent solution is preferably about 0.2% to about 1.0% (w/w).

Polymers

The polymer used as the binder in the reagent matrix should be sufficiently water-soluble and should also be capable of stabilizing and binding all other chemicals in the reagent to the conductive surface layer in the electrode area. Suitable polymers include, but are not limited to, low and high molecular weight polyethylene oxide (PEO), polyethylene glycol, polyvinyl pyrolidone, starch, methylcellulose, hydroxypropylcellulose, polyvinyl alcohol (PVA), carboxy methyl cellulose (CMC), and polyamino acids. The reagent binder may be a single polymer or a combination of polymers preferable in a concentration range of about 0.02% (w/w) to about 7.0% (w/w). The preferred binder in the reagent matrix of the present invention is a combination of polyethylene oxide (PEO) and methylcellulose. PEO's molecular weight ranges from thousands to millions and is available from Scientific Polymer Products, N.Y., USA. The concentration of PEO in the reagent mixture is preferably about 0.04% (w/w) to about 2% (w/w). Methylcellulose, which is available under the brand name of Methocel 60 HG (Cat. No. 64655, Fluka Chemicals, Milwaukee, Wis., USA) has a concentration in the reagent mixture preferably in the range of about 0.02% (w/w) to about 5% (w/w).

Surfactants

A surfactant may be optionally included in the reagent mixture to facilitate dispensing of the reagent mixture into the electrode areas. The amount and type of surfactant is selected to assure the previously mentioned functions and to avoid a denaturing effect on the enzymes. Surfactants can be selected from, but are not limited to, various anionic, cationic, non-ionic, and zwitterionic detergents. Examples of usable surfactants are polyoxyethylene ether, Tween 20, sodium cholate hydrate, hexadecylpyridinium cholide monohydrate and CHAPs. The preferred surfactant is a polyoxyethylene ether. More preferably, it is t-octylphenoxypolyethoxyethanol and is available under the brand name Triton X-100. The concentration of surfactant in the reagent mixture is preferably about 0.01% (w/w) to about 2% (w/w).

Buffer and Organic Solvents

Optionally, a buffer may be present along with a redox mediator in dried form in the reagent matrix of the sensor strip of the present invention. Examples of suitable buffers include citric acid, phosphates, Tris, and the like. In the present invention, the pH of the buffer is preferably in the range from about 5.0 to about 8.5. The phosphate buffer is the preferred buffer. Preferably, about a 1% to about a 5% organic solvent can be used to increase the solubility of organic electron mediators such as MB. The organic solvents can be chosen from, but not limited to, acetone, iso-propanol, DMF, DMSO, methylene chloride, and the like.

Bulking Reagent

An optional bulking agent that is water soluble and an inactive ingredient is preferably added into the reagent mixture. The use of a bulking agent is advantageous when a reagent layer 30 is used to contain the reagent matrix such that the electrode openings 32, 34, 36 in the reagent layer 30 will not trap bubbles when a sample fluid enters sample chamber 17. Various sugars such as, for example, trehalose, galactose, glucose, sucrose, lactose, mannitol, mannose, fructose, sucrose, lactose, lactitol, sorbitol, xylitol, nicotinamide, maltose, and the like, can be added into the reagent mixture as long as they do not react with other ingredients and are inactive at the electrode surface, i.e. the portion of the conductive path forming the electrode element. The bulking agent can be one chemical or a combination of chemicals. The amount of bulking agent in the reagent mixture is in the range from about 0.2% to about 15% (w/w).

Accordingly, the preferred reagent mixture (referred to below as "reagent mixture 1") used for the β-HB working electrode (W) and reference electrode (R) contains Methocel 60 HG, polyethylene oxide, MB, Triton X-100, bulking agents, HBDH enzyme, cofactor $NAD^+$ and phosphate buffer. The preferred reagent mixture (referred to below as "reagent mixture 2") used for the compensating electrode (C) contains Methocel 60 HG, polyethylene oxide, electron mediators MB or potassium ferricyanide, Triton X-100, bulking agents, and phosphate buffer.

Preparation of the Reagent Mixtures

Reagent mixture 1 is preferably prepared in two steps, although it can be prepared in one step:

Step 1: Into phosphate buffer, add Methocel 60 HG, polyethylene oxide, methylcellulose, bulking agent, and Triton X-100 in amounts within the preferred concentration ranges previously disclosed. Stir the solution until dissolved using a magnetic stirrer.

Step 2: Into the above Step 1 solution, add MB, enzyme HBDH and co-factor $NAD^+$ in amounts within the preferred concentration ranges previously disclosed. Stir the solution until dissolved. The resulting solution is ready for application to the working and reference electrode elements.

Reagent mixture 2 is prepared in two steps:

Step 3: Into phosphate buffer, add Methocel 60 HG, polyethylene oxide, bulking agent, and Triton X-100 in amounts within the preferred concentration ranges previously disclosed. Stir the solution until dissolved using a magnetic stirrer.

Step 4: Into the above Step 3 solution, add potassium ferricyanide or MB in amounts within the preferred concentration ranges previously disclosed. Stir the solution until dissolved. The resulting solution is ready for application to the compensating electrode element.

The chemical reagents incorporated into the electrodes can also be done through screen-printed techniques or the like. Screen-printed electrodes incorporated with MB were produced from an organic carbon ink containing, HBDH, $NAD^+$ enzyme co-factor and a polysaccharide binder. The solid powder MB or MB solution were mixed into commercial conducting carbon ink or carbon paste.

Sensor Construction

Assembly of the various preferred embodiments of the present invention is relatively straightforward. Generally for the 4-layer configuration, the base layer 20 and reagent layer 30 are laminated to each other followed by dispensing a predefined quantity of the appropriate reagent mixture into each of the electrode openings 32, 34, 36. After drying the reagent mixture, the channel layer 40 is disposed onto the reagent layer 30 and the cover 50 is then disposed onto the channel layer 40. For the 3-layer construction, the base layer 20 and the channel layer 40 are laminated to each other followed by dispensing the appropriate reagent mixture as distinct drops/droplets into the U-shaped channel notch 42 onto their respective conductive surface areas. After drying the reagent mixture, the cover 50 is then disposed onto the channel layer 40.

More particularly, a piece of a gold polyester film is cut to the shape illustrated in FIG. 2, forming base layer 20 of sensor 10. A laser (previously disclosed) is used to score the gold polyester film. As illustrated in FIG. 2, the film is scored by the laser such that three electrodes at sample fluid end 14 and three contact points 22, 24 and 26 are formed at electrical contact end 16. The scoring line is very thin but sufficient to create three separate electrical paths. A scoring line 28 may optionally be made, but is not necessary, along the outer edge of base layer 20 to avoid potential static problems which could cause a noisy signal from the finished sensor 10.

A piece of one-sided adhesive tape is then cut to size and shape, forming reagent layer 30 so that it will cover a major portion of conductive layer 21 of base layer 20 except for exposing a small electrical contact area illustrated in FIG. 1 by reference number 16.

Before attaching reagent layer 30 to base layer 20, three circular openings 32, 34 and 36 of substantially equal size are punched by laser, or by mechanical means such as a die-punch assembly, creating electrode openings 32, 34 and 36 in reagent layer 30. The preferred hole size for openings 32, 34 and 36 has a typical diameter of about 0.030 in. (0.76 mm). As illustrated in FIG. 2, electrode openings 32, 34 and 36 are aligned with each other and have a spacing of about 0.020 in. (0.508 mm) to about 0.050 in. (1.27 mm) between adjacent openings. The circular shape of the electrode openings are for illustrative purposes only. It should be understood that the shape and size of the electrode openings or the distance between them is not critical. The circular openings do not have to be substantially equal in size so long as the ratio of the surface areas remains substantially constant. As stated previously, the preferred arrangement of the electrodes formed in electrode openings 32, 34 and 36 is W (working electrode), R (reference electrode) and C (compensating electrode). Reagent layer 30 is then attached to base layer 20 in such a way as to define the electrode wells W, R and C.

Reagent mixture 1 is dispensed into the working and reference electrode areas W and R. As described above, reagent mixture 1 is preferably a mixture of a bulking agent, a polymer binder, a surfactant, a redox mediator, an enzyme, an enzyme co-factor and a buffer. Similarly, Reagent mixture 2 is dispersed into compensating electrode area C.

After dispensing the reagents in their respective electrode areas, the reagents are dried at a temperature in the range of about room temperature to about 60° C. The length of time required to dry the reagents is dependent on the temperature at which the drying process is performed.

After drying, a piece of double-sided tape available from Adhesive Research or GIC is fashioned into channel layer 40 containing U-shaped channel notch 42. Channel layer 40 is then layered onto reagent layer 30. As mentioned earlier, channel layer 40 serves as a spacer and defines the size of sample chamber 17.

A piece of a transparency film available from 3M or from GIC is fashioned into top layer 50. A vent opening 52 is made using the laser previously mentioned or by means of a die-punch. Vent opening 52 is located approximately 0.180 in. (4.57 mm) from fluid entrance 54. Cover 50 is aligned and disposed onto channel layer 40 to complete the assembly of β-HB sensor 10, as illustrated in FIG. 1.

Testing the β-HB Sensor

When a fluid sample is applied to a single β-HB sensor 10 of the present invention, the fluid sample enters the sample chamber 17 through the sampling inlet 18 and flows over the W, R and C electrodes by capillary action and stops at the threshold of the vent opening 52.

Amperometry was used for measurement of the current response of the β-HB sensor using an Electrochemical Analyzer (Model 812, CH Instruments, Austin, Tex., USA). Once a blood sample enters the sensor 10, a potential of −0.05 to +0.30 volts (depending on reference electrode used) is applied across the working/compensating electrodes W, C and the reference electrode R. The β-HB concentration of the same blood sample is measured with Stanbio Laboratory—hydroxybutyrate liquicolor Reagent kits on Perkin-Elmer 552 spectrophotometer.

The above-described embodiments are based on amperometric analyses. Those skilled in the art, however, will recognize that a sensor of the invention may also utilize coulometric, potentiometric, voltammetric, and other electrochemical techniques to determine the concentration of an analyte in a sample.

The following test protocols illustrate the unique features of the sensor of the present invention that uses a redox mediator that is considered an enzyme inhibitor.

Example 1

Determination of β-HB concentration was conducted using the β-HB sensor test strips described above. The reference electrode R incorporates electron mediator MB as the reference electrode material and the applied potential between the working electrode W and the reference electrode R is about 250 mV.

Blood samples containing different β-HB concentrations were tested with the β-HB sensors described above using the above-described reagent formulations. Table 1 shows the corrected current response in nanoamps in blood samples with varying levels of β-HB. The corrected current response means the differential current response between the working electrode and the compensating electrode.

TABLE 1

Linearity

| β-HB concentration (mM) | Corrected current response (nA) |
|---|---|
| 0.1 | 0.5 |
| 1.2 | 3.1 |
| 2.2 | 6.6 |
| 3.4 | 8.4 |
| 4.5 | 11.2 |
| 5.2 | 13.3 |
| 6.4 | 15.6 |
| 7.6 | 17.4 |

Figure 6:
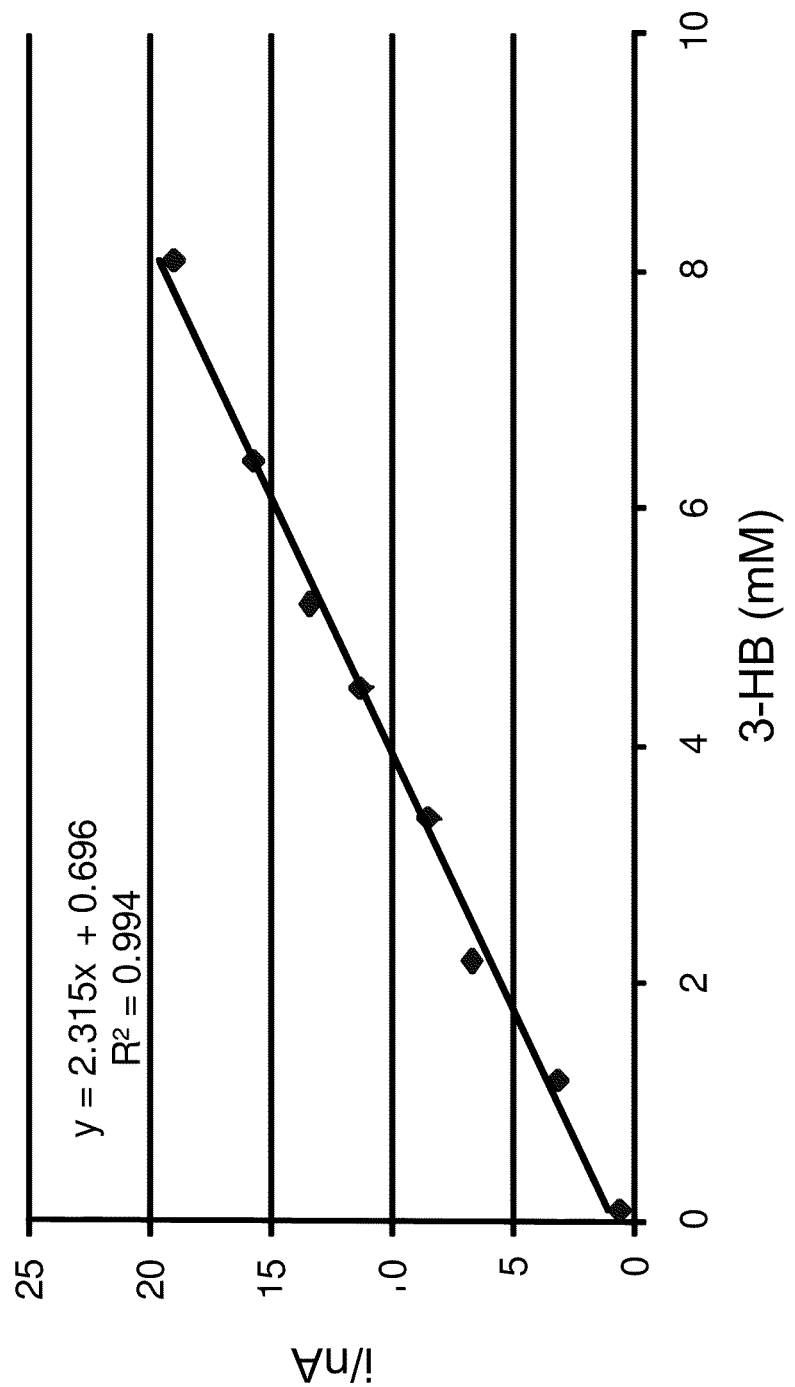
FIG. 6 illustrates the correlation between the current responses of the β-HB sensor of the present invention to β-HB concentrations where the reference material in the strip is MB.

A graphical illustration of the test data is shown in FIG. 6. The test results demonstrate that the β-HB sensor of the present invention has a linear response (current response vs. β-HB concentration) over a β-HB concentration range from about 0.1 mM to about 8 mM.

Example 2

Precision of β-HB Sensor

The precision of the β-HB sensor of present invention was investigated using two concentration levels of β-HB (1.7 mM and 3.8 mM) in blood samples. Table 2 shows the precision of the β-HB sensor of the present invention. A total of 10 measurements using the β-HB sensors were made on each level of β-HB blood sample.

TABLE 2

Precision

| | Strip readings (mM) | |
| measurements | 1.7 mM | 3.8 mM |
|---|---|---|
| 1 | 1.5 | 3.5 |
| 2 | 1.5 | 3.9 |
| 3 | 1.9 | 3.7 |
| 4 | 1.6 | 3.9 |
| 5 | 1.6 | 3.6 |
| 6 | 1.7 | 3.8 |
| 7 | 1.4 | 3.7 |
| 8 | 1.5 | 3.6 |
| 9 | 1.8 | 3.5 |
| 10 | 1.6 | 3.4 |
| Mean (mM) | 1.6 | 3.7 |
| S.D | 0.15 | 0.17 |

Figure 7:
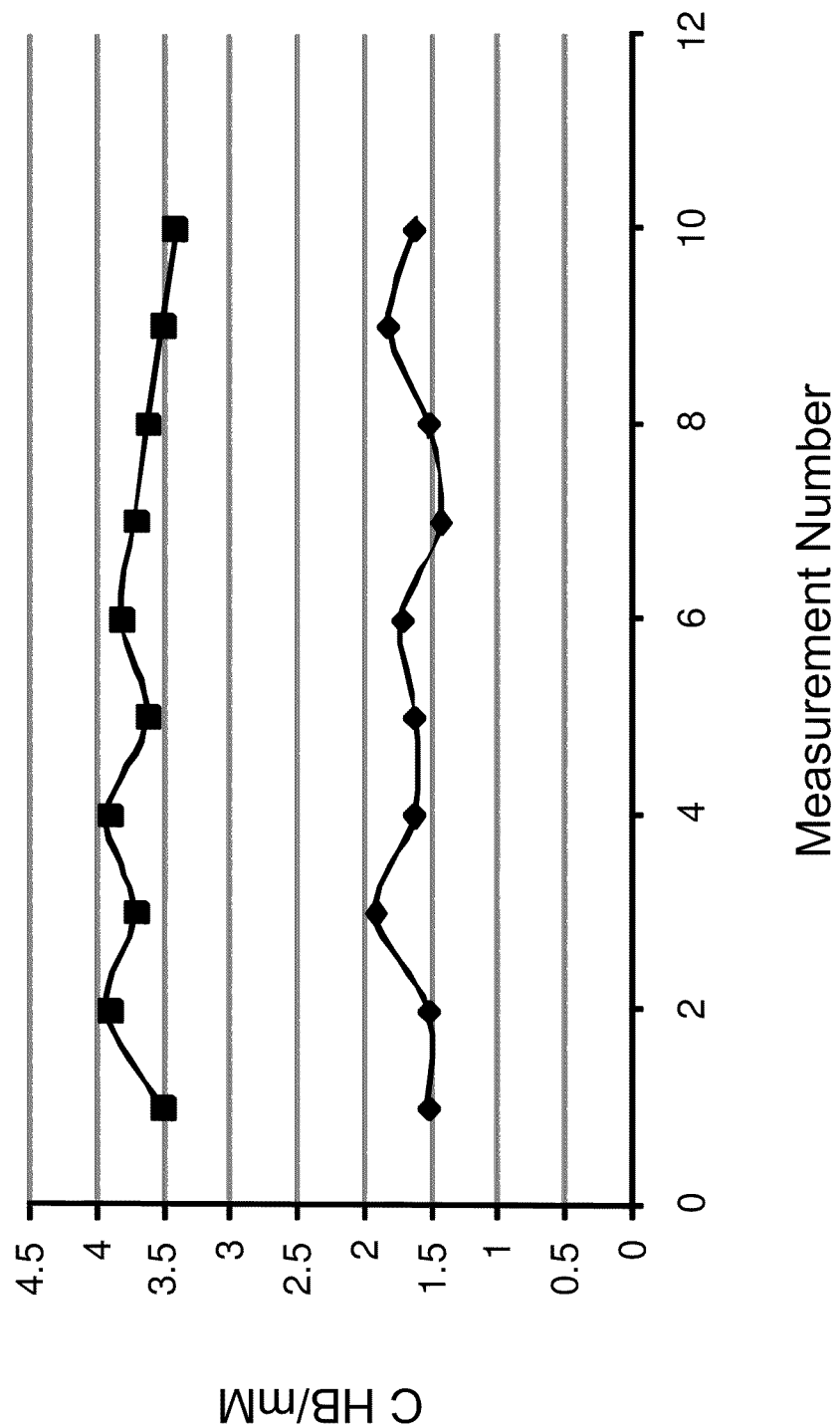
FIG. 7 illustrates the precision of the β-HB sensor of the present invention at two different β-HB concentrations where the concentrations of β-HB are 1.7 mM and 3.8 mM separately.

A graphical illustration of the test data is shown in FIG. 7.

Example 3

Determination of β-HB concentration was conducted using the β-HB sensor strips described above. The reference electrode R incorporates the electron mediator potassium ferricyanide as the reference electrode material and an applied potential between the working electrode W and the reference electrode R is about −50 mV.

Blood samples with different β-HB concentrations were tested with the β-HB sensors described above with above-described reagent formulations. Table 3 shows the current response in nanoamps in a blood sample with varying levels of β-HB.

TABLE 3

Linearity

| β-HB concentration (mM) | Current response (nA) |
|---|---|
| 0.2 | 0.6 |
| 1.5 | 3.4 |
| 3.4 | 8.1 |
| 4.6 | 10.1 |
| 6.5 | 13.7 |
| 8.0 | 17.0 |

Figure 8:
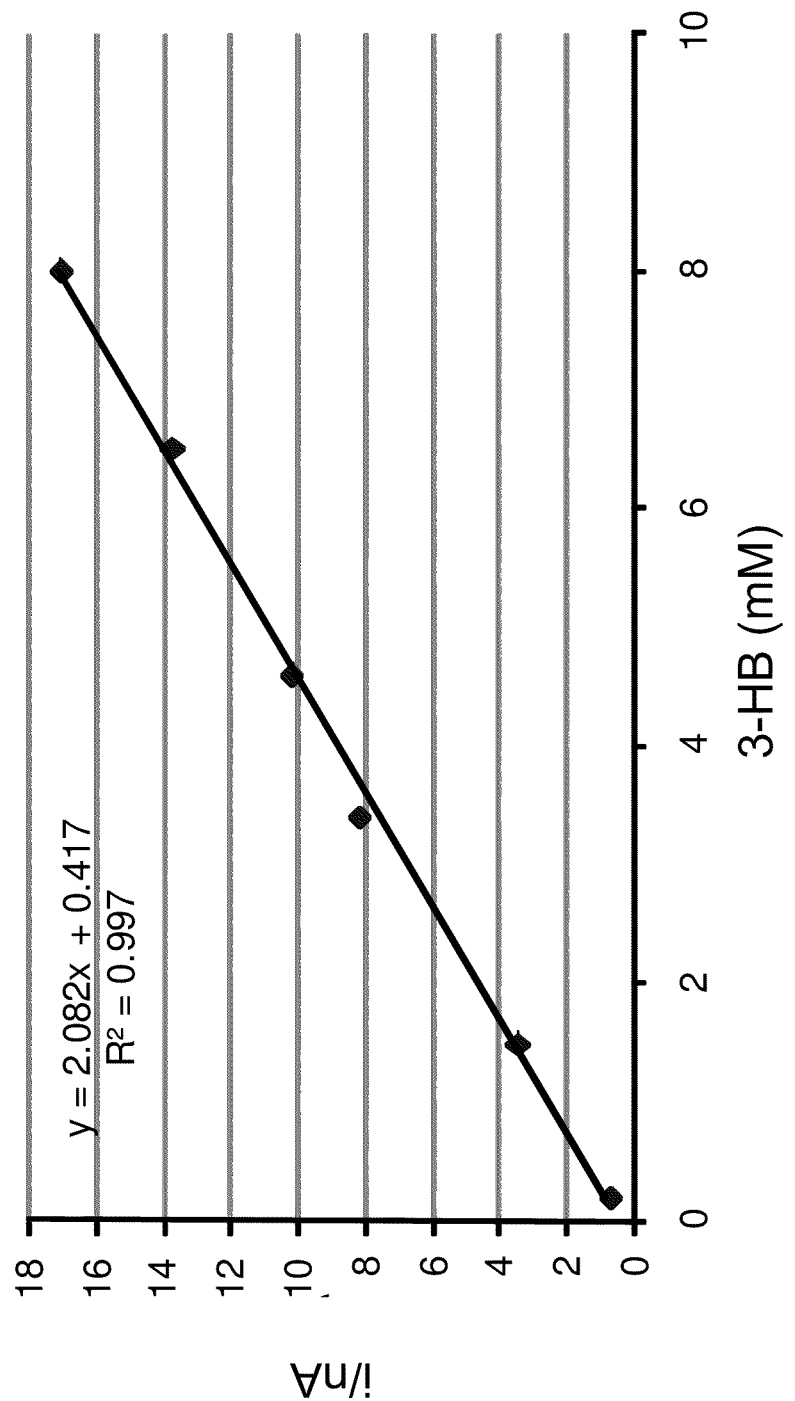
FIG. 8 illustrates the correlation between the current responses of the β-HB sensor of the present invention to β-HB concentration where the reference material is potassium ferricyanide.

A graphical illustration of the test data is shown in FIG. 8. The test results demonstrate that the β-HB sensor of the present invention has a linear response (current response vs. β-HB concentration) over a β-HB concentration range from about 0.2 mM to about 8 mM.

Example 4

Evaluation of the shelf life stability of sensors incorporating an irreversible enzyme inhibitor such as Meldola's Blue in dry strips containing HBDH and $NAD^+$.

In this study, two differently aged β-HB sensor strips were used for the study to evaluate the shelf life stability of the β-HB sensor. One batch of β-HB sensor strips was stored at room temperature for 6 months (strips A) and another batch of β-HB sensor strips was freshly prepared (strips B). Blood samples with different β-HB concentrations were tested using these two batches of β-HB sensor strips and the results are shown in the Table 4. Each concentration result is an average of five measurements, one measurement per β-HB sensor.

TABLE 4

Comparison of shelf life stability of β-HB sensor strips

| Strip A (six months) (mM) | Strip B (freshly prepared) (mM) |
|---|---|
| 0.3 | 0.2 |
| 1.6 | 1.7 |
| 2.8 | 2.8 |
| 3.7 | 3.7 |
| 4.9 | 5.1 |
| 5.7 | 5.8 |
| 6.7 | 6.6 |

Figure 9:
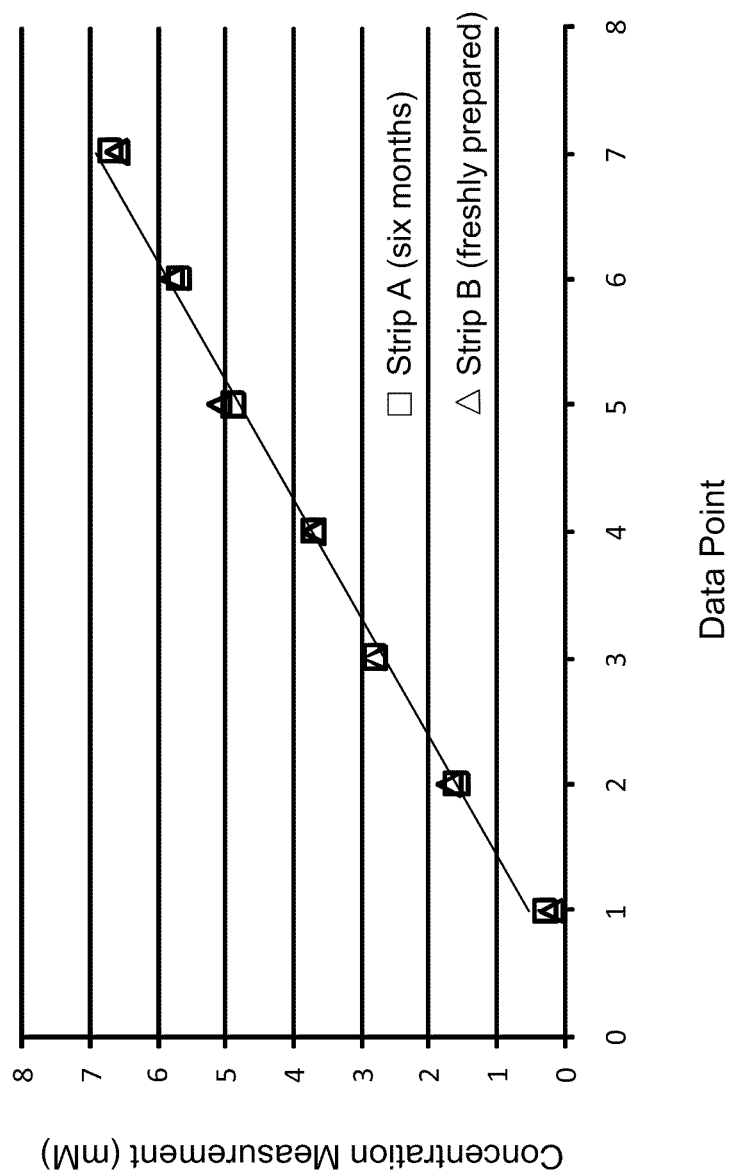
FIG. 9 illustrates the data measurement comparison for different values of β-HB between freshly made β-HB sensors of the present invention to 6-month old β-HB sensors.

A graphical illustration of the test data is shown in FIG. 9. The test results demonstrate that the reagent matrix is relatively stable over time so that the β-HB sensor test strips containing the reagent matrix described above with the mediator considered an irreversible enzyme inhibitor can be stored for extended periods and then used to provide relatively accurate determinations of the levels of β-HB in liquid samples.

Example 5

Determination of ethanol concentration was conducted using ethanol sensor test strips prepared in a similar manner. Reagent mixture which is dispensed into the working electrode area is preferably a mixture of a bulking agent, a polymer binder, a surfactant, meldolas's blue as a redox mediator, NAD as an enzyme co-factor, alcohol dehydrogenase as an enzyme and buffer solution. The reagents dispensed in reference and compensating electrodes areas are similar as those in the working area but without alcohol enzyme. Blood samples containing different ethanol concentrations were tested with the ethanol test. Table 5 shows the current response in nanoamps in a blood sample with varying levels of ethanol (percentage).

TABLE 5

Linearity

| Ethanol concentration (%) | Corrected response current (nA) |
|---|---|
| 0.01 | 1.30 |
| 0.05 | 3.02 |
| 0.1 | 4.62 |
| 0.2 | 6.06 |
| 0.3 | 7.58 |
| 0.4 | 9.30 |
| 0.5 | 10.96 |

Figure 10:
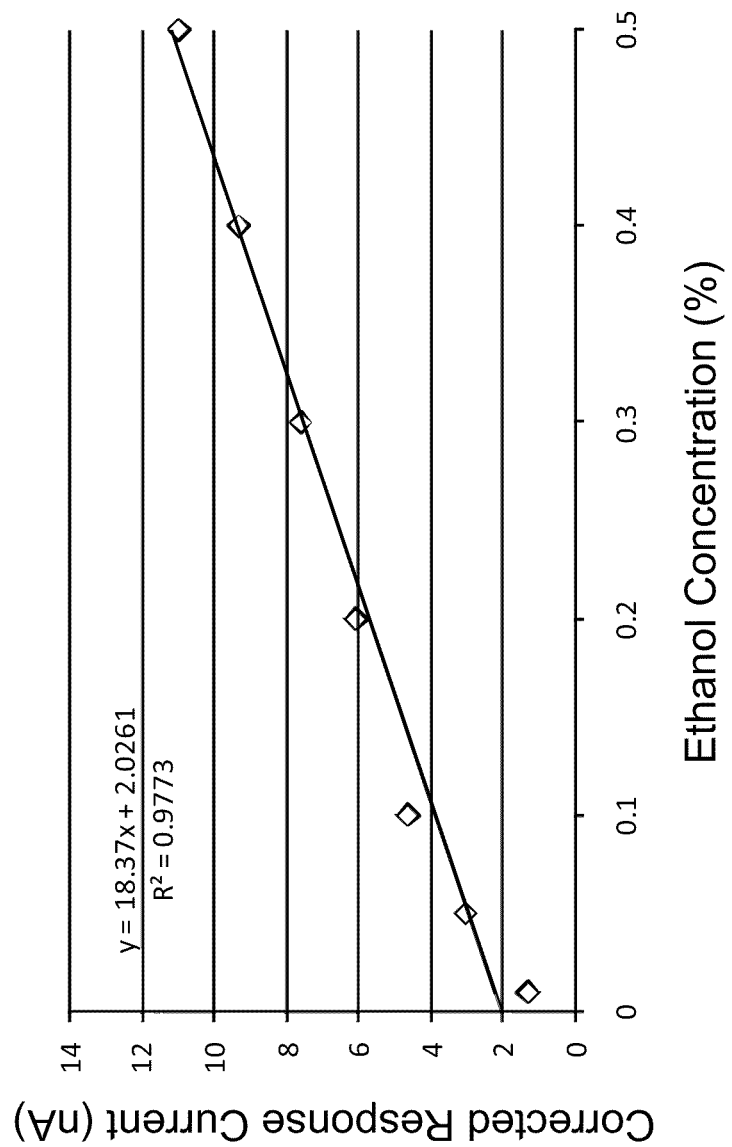
FIG. 10 illustrates the correlation between the current responses of the ethanol sensor of the present invention to ethanol concentrations.

A graphical illustration of the test data is shown in FIG. 10. The test results demonstrate that the ethanol sensor of the present invention has a linear response (current response vs. ethanlol concentration in percent) over a ethanol concentration range from about 0.01% to about 0.5%.

Example 6

Determination of cholesterol concentration was conducted using cholesterol sensor test strips prepared in a similar manner. Reagent mixture which is dispensed into the working electrode area, is preferably a mixture of a bulking agent, a polymer binder, a surfactant, meldolas's blue as a redox mediator, NAD as an enzyme co-factor, cholesterol esterase and cholesterol dehydrogenase as enzymes, and buffer solution. The reagents dispensed in reference and compensating electrodes areas are similar as those in the working area but without cholesterol esterase and cholesterol dehydrogenase as enzymes. Blood samples containing different cholesterol concentrations were tested with the cholesterol test strips and the results showed a linear response to the concentration of cholesterol.

The present invention is not limited to the measurement of β-hydroxybutyrate, but is useful for measuring other substances involving the enzyme reaction of NAD(P)-dependent dehydrogenase. Those other substances/species include, but are not limited to, glucose dehydrogenase for glucose, glucose 6-phosphate dehydrogenase for glucose 6-phosphate, β-hydroxybutyrate dehydrogenase to β-hydroxybutyrate, cholesterol dehydrogenase for cholesterol, lactate dehydrogenase for lactate, alcohol dehydrogenase for ethanol, glycerol dehydrogenase for glycerol, malate dehydrogenase for malate and fructose dehydrogenase for fructose.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A method for determining information indicative of the level of an analyte in a liquid sample, the method comprising:
reacting the liquid sample with a working electrode having a reagent matrix disposed thereon, the reagent matrix formed from a dispensing reagent containing an enzyme capable of catalyzing a reaction involving the analyte, a mediator that is considered an enzyme inhibitor, and an enzyme co-factor wherein the mediator is selected from the group consisting of meldola's blue, 4-methyl-1,2-benzoquinone, and 2,6-dichloroindophenol, the enzyme co-factor having a concentration in the dispensing reagent of about 0.01% to about 3.0% (w/w) and the mediator having a concentration in the dispensing reagent of about 0.05% to about 3.0% (w/w), wherein the working electrode provides a stable and sensitive response when the working electrode is stored at ambient conditions for a period of time of at least 3 months or longer;
generating an electrical output from the reagent matrix;
measuring the electrical output; and
determining the level of the analyte in the liquid sample using information comprising the measured electrical output.

2. The method of claim 1 wherein the reacting step further includes forming the reagent matrix by dissolving the enzyme, the mediator and the enzyme co-factor in an aqueous solvent forming a dispensing reagent wherein the amount of the enzyme co-factor to the mediator in the dispensing reagent is a ratio in the range of about 0.01:1 to 15:1.

3. The method of claim 2 wherein the dissolving step further includes dissolving an amount of the enzyme co-factor that is in the range of about 0.1% to about 0.6% (w/w) of the dispensing reagent.

4. The method of claim 3 wherein the dissolving step further includes selecting the enzyme co-factor from one of $NAD^+$ and $NADP^+$.

5. The method of claim 1 wherein the dissolving step further includes dissolving an amount of the mediator that is in the range of about 0.2% to about 1.0% (w/w) of the dispensing reagent.

6. A biosensor for measuring an analyte in a liquid sample, the biosensor comprising:
a working electrode having a reagent matrix formed from a dispensing reagent containing an enzyme capable of catalyzing a reaction involving the analyte, a mediator that is considered as an enzyme inhibitor, and an enzyme co-factor wherein the mediator is selected from the group consisting of meldola's blue, 4-methyl-1,2-benzoquinone, and 2,6-dichloroindophenol, the enzyme co-factor having a concentration in the dispensing reagent of about 0.01% to about 3.0% (w/w) and the mediator having a concentration in the dispensing reagent of about 0.05% to about 3.0% (w/w) or less, wherein the working electrode provides a stable and sensitive response even when the biosensor is stored at ambient conditions for a period of time selected from the group consisting of at least 3 months, 12 months and two years or more; and
a reference electrode.

7. The biosensor of claim 6 wherein a ratio of the enzyme co-factor to the mediator is in the range of about 0.01:1 to 15:1.

8. The biosensor of claim 1 wherein the mediator has a concentration in the dispensing reagent of about 0.05% to about 2% (w/w).

9. The biosensor of claim 1 wherein the enzyme co-factor has a concentration in the dispensing reagent of about 0.1% to about 0.6% (w/w).

10. The biosensor of claim 9 wherein the enzyme co-factor is one of $NAD^+$ and $NADP^+$.

11. The biosensor of claim 1 wherein the mediator has a concentration in the dispensing reagent of about 0.2% to about 1.0% (w/w).

12. The biosensor of claim 1 wherein the enzyme is selected from one of glucose dehydrogenase, glucose 6-phosphate dehydrogenase, β-hydroxybutyrate dehydrogenase, cholesterol dehydrogenase, lactate dehydrogenase, alcohol dehydrogenase, glycerol dehydrogenase, malate dehydrogenase, and fructose dehydrogenase.

13. The biosensor of claim 1 further comprising:
a laminated body having a sample inlet end and an electrical contact end;
a sample inlet;
a substantially flat sample chamber in communication with the sample inlet, the test chamber being adapted to collect a fluid sample through the sample inlet wherein the working electrode and the reference electrode are located within the sample chamber.

14. The biosensor of claim 13 further comprising a compensating electrode within the sample chamber and used in conjunction with the working electrode, the reference electrode or both to negate any interferent species effects from interferent species in the sample.

15. A biosensor for measuring an analyte in a liquid sample, the biosensor comprising:
a working electrode having a reagent matrix formed from a dispensing reagent containing a mediator that is considered an enzyme inhibitor, an enzyme and an enzyme co-factor wherein the mediator is selected from the group consisting of meldola's blue, 4-methyl-1,2-benzoquinone, and 2,6-dichloroindophenol, the enzyme co-factor having a concentration in the dispensing reagent of about 0.01% to about 3.0% (w/w) and the mediator having a concentration in the dispensing reagent of about 0.05% to about 3.0% (w/w), wherein the working electrode is configured for producing a stable and sensitive response when the biosensor is stored at ambient conditions for 3 months or longer; and
a reference electrode.

16. The biosensor of claim 15 wherein the enzyme co-factor has a concentration in the dispensing reagent in a range of about 0.1% to about 0.6% (w/w) and the mediator has a concentration in the dispensing reagent in a range of about 0.05% to about 2% (w/w).

17. The biosensor of claim 15 wherein the enzyme co-factor has a concentration in the dispensing reagent in a range of about 0.1% to about 0.6% (w/w) and the mediator has a concentration in the dispensing reagent in a range of about 0.2% to about 1% (w/w).

18. A biosensor for measuring an analyte in a liquid sample, the biosensor comprising:
a working electrode having a reagent matrix formed from a dispensing reagent containing a mediator that is considered an enzyme inhibitor, an enzyme and an enzyme co-factor wherein the mediator is selected from the group consisting of meldola's blue, 4-methyl-1,2-benzoquinone, and 2,6-dichloroindophenol, the enzyme co-factor having a concentration in the dispensing reagent of about 0.01% to about 3.0% (w/w) and the mediator having a concentration in the dispensing reagent of about 0.05% to about 3.0% (w/w), wherein the enzyme co-factor and the mediator are present in the dispensing reagent that is used to form the reagent matrix in a ratio that enables the working electrode to produce a stable and sensitive response when the biosensor is stored at ambient conditions for 3 months or longer; and
a reference electrode.

19. The biosensor of claim 18 wherein the enzyme co-factor has a concentration in the dispensing reagent in a range of about 0.1% to about 0.6% (w/w) and the mediator has a concentration in the dispensing reagent in a range of about 0.05% to about 2% (w/w).

20. The biosensor of claim 18 wherein the enzyme co-factor has a concentration in the dispensing reagent in a range of about 0.1% to about 0.6% (w/w) and the mediator has a concentration in the dispensing reagent in a range of about 0.2% to about 1% (w/w).

21. A biosensor based on NAD(P)-dependent dehydrogenase enzymes, the biosensor comprising:
a working electrode having a reagent matrix formed from a dispensing reagent containing a mediator that is considered an enzyme inhibitor, NAD(P)-dependent dehydrogenase enzymes and an enzyme co-factor wherein the mediator is selected from the group consisting of meldola's blue, 4-methyl-1,2-benzoquinone, and 2,6-dichloroindophenol, the enzyme co-factor having a concentration in the dispensing reagent of about 0.01% to about 3.0% (w/w) and the mediator having a concentration in the dispensing reagent of about 0.05% to about 3.0% (w/w), wherein the working electrode is capable of measuring the concentration of an analyte in a liquid sample without calibrating the working electrode; and
a reference electrode.

22. The biosensor of claim 21 wherein the NAD(P)-dependent dehydrogenase enzymes have a concentration in the dispensing reagent in a range of about 0.1% to about 0.6% (w/w) and the mediator has a concentration in the dispensing reagent in a range of about 0.05% to about 2% (w/w).

23. The biosensor of claim 21 wherein the NAD(P)-dependent dehydrogenase enzymes and the mediator are in a ratio in the range of about 0.01:1 to 15:1.

24. The biosensor of claim 21 wherein the NAD(P)-dependent dehydrogenase enzymes have a concentration in the dispensing reagent in a range of about 0.1% to about 0.6% (w/w).

25. The biosensor of claim 21 wherein the mediator has a concentration in the dispensing reagent in a range of about 0.2% to about 1% (w/w).

26. A method of making a biosensor for measuring an analyte in a liquid sample where the biosensor has a mediator considered to be an enzyme inhibitor and is capable of long term storage, the method comprising:
forming a working electrode and a reference electrode on a substrate;
formulating a dispensing reagent containing an enzyme capable of catalyzing a reaction involving the analyte, a mediator that is considered an enzyme inhibitor, and an enzyme co-factor wherein the mediator is selected from the group consisting of meldola's blue, 4-methyl-1,2-benzoquinone, and 2,6-dichloroindophenol, the enzyme co-factor having a concentration in the dispensing reagent of about 0.01% to about 3.0% (w/w) and the mediator having a concentration in the dispensing reagent of about 0.05% to about 3.0% (w/w), wherein the ratio of the enzyme co-factor and the mediator in the dispensing reagent enables the working electrode to have a stable response when the biosensor is stored at ambient conditions for 3 months or longer;
dispensing a quantity of the dispensing reagent onto the working electrode; and
evaporating the dispensing reagent forming a reagent matrix on the working electrode.

27. The method of claim 26 wherein the formulating step includes dissolving an amount of the enzyme co-factor and the mediator in the dispensing reagent, the amount being a ratio in the range of about 0.01:1 to about 15:1 of the enzyme co-factor to the mediator.

28. The method of claim 26 wherein the dissolving step further includes dissolving an amount of the enzyme co-factor that is in the range of about 0.1% to about 0.6% (w/w) of the dispensing reagent.

29. The method of claim 26 wherein the dissolving step further includes selecting the enzyme co-factor from one of $NAD^+$ and $NADP^+$.

30. The method of claim 26 wherein the dissolving step further includes dissolving an amount of the mediator that is in the range of about 0.2% to about 1.0% (w/w) of the dispensing reagent.

\* \* \* \* \*